(12) United States Patent
Stier

(10) Patent No.: US 6,582,682 B2
(45) Date of Patent: Jun. 24, 2003

(54) ORAL CARE COMPOSITIONS COMPRISING STABILIZED CHLORINE DIOXIDE

(75) Inventor: Roger E. Stier, Clifton, NJ (US)

(73) Assignee: Noville, Inc., South Hackensack, NJ (US)

(*) Notice: Subject to any disclaimer, the term of this patent is extended or adjusted under 35 U.S.C. 154(b) by 0 days.

(21) Appl. No.: 10/230,923

(22) Filed: Aug. 29, 2002

(65) Prior Publication Data

US 2002/0197215 A1 Dec. 26, 2002

Related U.S. Application Data

(63) Continuation-in-part of application No. 09/699,737, filed on Oct. 30, 2000, now abandoned.

(51) Int. Cl.[7] ............................. A61K 7/16; A61K 7/20; A61K 51/12; B01F 17/00; B01J 13/02
(52) U.S. Cl. ..................... 424/53; 424/49; 424/661; 424/613; 424/489; 424/52; 426/533; 426/534; 516/53; 264/4.1
(58) Field of Search .................... 424/49–58, 489, 424/661; 426/533, 534

(56) References Cited

U.S. PATENT DOCUMENTS

| | | | | |
|---|---|---|---|---|
| 4,146,499 A | * | 3/1979 | Rosano ...................... 252/186 |
| 4,330,531 A | | 5/1982 | Alliger |
| 4,585,482 A | * | 4/1986 | Tice et al. .................. 424/665 |
| 4,689,215 A | | 8/1987 | Ratcliff |
| 4,696,811 A | | 9/1987 | Ratcliff |
| 4,786,492 A | | 11/1988 | Ratcliff |
| 4,788,053 A | | 11/1988 | Ratcliff |
| 4,792,442 A | | 12/1988 | Ratcliff |
| 4,793,989 A | | 12/1988 | Ratcliff |
| 4,808,389 A | | 2/1989 | Ratcliff |
| 4,818,519 A | | 4/1989 | Ratcliff |
| 4,835,002 A | * | 5/1989 | Wolf et al. ................. 426/590 |
| 4,837,009 A | | 6/1989 | Ractliff |
| 4,851,213 A | | 7/1989 | Ratcliff |
| 4,855,135 A | | 8/1989 | Ratcliff |
| 4,861,514 A | * | 8/1989 | Hutchings .................. 510/102 |
| 4,889,714 A | | 12/1989 | Ratcliff |
| 4,891,216 A | | 1/1990 | Kross et al. |
| 4,902,498 A | * | 2/1990 | Agricola et al. .............. 424/52 |
| 4,925,656 A | | 5/1990 | Ratcliff |
| 4,963,287 A | * | 10/1990 | Hutchings et al. .......... 510/101 |
| 4,971,788 A | * | 11/1990 | Tabibi et al. ................. 424/49 |
| 4,975,285 A | | 12/1990 | Ratcliff |
| 4,978,535 A | | 12/1990 | Ractliff |
| 4,986,990 A | | 1/1991 | Davidson et al. |
| 4,992,276 A | * | 2/1991 | Dills ............................ 424/49 |
| 5,019,402 A | | 5/1991 | Kross et al. |
| 5,100,652 A | * | 3/1992 | Kross et al. .................. 424/53 |
| 5,130,122 A | * | 7/1992 | Tabibibi et al. ............... 424/49 |
| 5,200,171 A | | 4/1993 | Ratcliff |
| 5,281,412 A | * | 1/1994 | Lukacovic et al. ............ 424/52 |
| 5,283,056 A | * | 2/1994 | Chung et al. ................. 424/49 |
| 5,292,527 A | * | 3/1994 | Konopa ....................... 424/54 |
| 5,320,863 A | * | 6/1994 | Chung et al. ............... 426/650 |
| 5,328,682 A | * | 7/1994 | Pullen et al. ................. 424/49 |
| 5,348,734 A | | 9/1994 | Ratcliff |
| 5,374,614 A | * | 12/1994 | Behan et al. .................. 512/3 |
| 5,444,041 A | * | 8/1995 | Owen et al. ................ 424/400 |
| 5,468,725 A | * | 11/1995 | Guenin et al. ................ 512/3 |
| 5,489,435 A | | 2/1996 | Ratcliff |
| 5,514,366 A | * | 5/1996 | Diamond ...................... 424/49 |
| 5,585,343 A | * | 12/1996 | McGee et al. ................ 512/1 |
| 5,605,651 A | * | 2/1997 | Balzer ........................ 424/401 |
| 5,618,550 A | | 4/1997 | Ratcliff |
| 5,628,986 A | * | 5/1997 | Sanker et al. ................. 424/49 |
| 5,633,226 A | * | 5/1997 | Owen et al. ................. 424/400 |
| 5,646,109 A | * | 7/1997 | Owen et al. ................. 424/400 |
| 5,662,888 A | * | 9/1997 | Diamond ..................... 424/49 |
| 5,707,648 A | * | 1/1998 | Yiv ............................ 424/450 |
| 5,736,505 A | * | 4/1998 | Manzo et al. ............... 424/401 |
| 5,772,986 A | * | 6/1998 | Kross .......................... 424/53 |
| 5,827,522 A | * | 10/1998 | Nowak ....................... 424/400 |
| 6,017,515 A | | 1/2000 | van den Bosch |
| 6,071,539 A | * | 6/2000 | Robinson et al. |
| 6,077,502 A | * | 6/2000 | Witt et al. |
| 6,086,372 A | * | 7/2000 | Diamond .................... 433/216 |
| 6,117,415 A | * | 9/2000 | Schwarz ...................... 424/49 |
| 6,132,702 A | * | 10/2000 | Witt et al. .................... 424/53 |
| 6,306,372 B1 | * | 10/2001 | Stier et al. ................... 424/49 |
| 6,407,051 B1 | * | 6/2002 | Smith et al. ................ 510/417 |

FOREIGN PATENT DOCUMENTS

| | | |
|---|---|---|
| DE | 2 329 753 | 12/1973 |
| EP | 0 565 134 B1 | 3/1996 |
| GB | 2 289 841 A | 12/1995 |
| JP | 60054311 | 3/1985 |
| JP | 60105610 | 6/1985 |
| WO | WO 89/03179 | 4/1989 |
| WO | WO 95/27472 | 10/1995 |

* cited by examiner

Primary Examiner—Shep K. Rose
(74) Attorney, Agent, or Firm—Norris McLaughlin & Marcus

(57) ABSTRACT

Oral care compositions comprising chlorine dioxide and excipients, including flavoring agents and ethoxylated hydrogenated castor oil having ethoxylation numbers from about 35 to about 60. The flavoring agents become bound to the hydrophobic end of the ethoxylated hydrogenated castor oil molecule and become encapsulated within the molecule as the hydrophilic end of the ethoxylated hydrogenated castor oil wraps around the flavoring agent. The flavoring agent does not undergo oxidation. The oral care compositions do not develop either a chlorine odor or yellowing discoloration. The oral care compositions can be packaged, stored, sold and used in a single package.

21 Claims, No Drawings

ORAL CARE COMPOSITIONS COMPRISING STABILIZED CHLORINE DIOXIDE

CROSS REFERENCE TO RELATED APPLICATIONS

This application is a continuation-in-part of U.S. patent application Ser. No. 09/699,737 filed Oct. 30, 2000, which is now abandoned.

BACKGROUND OF THE INVENTION

1. Field of the Invention

The invention relates to oral care compositions, and methods for making the oral care compositions, comprising chlorine dioxide, and excipients, including flavoring agents and ethoxylated hydrogenated castor oils having ethoxylation numbers from about 35 to about 60. The flavoring agents become bound to the hydrophobic side of the ethoxylated hydrogenated castor oil in a microemulsion, and become microencapsulated as the hydrophilic side of the ethoxylated hydrogenated castor oil wraps around the flavoring agent thus stabilizing the flavoring agent against oxidation from residual chlorine in the solution. Therefore, oral care compositions of the invention do not have yellowing discoloration or exhibit chlorine odor and can be packaged, stored, sold and used in a single package.

2. The Prior Art

Oral malodor, plaque, gingivitis, periodontal disease, and discoloration of the teeth, are all undesirable conditions that affect many people. Malodor of the oral cavity is also known as halitosis or bad breath and it is generally believed that the cause of this condition is due to the presence of anaerobic bacteria, especially gram-negative anaerobic bacteria, in the mouth. These bacteria will generate volatile sulfur compounds (VSC) which are known to cause breath malodor.

Some breath malodor is caused by three chemical compounds. Specifically, hydrogen sulfide (H—S—H), methyl mercaptan ($CH_3$—S—H) and dimethyl sulfide $CH_3$—S—$CH_3$. These compounds result from the degradation of epithelial cells and bacteria in the oral cavity. The polypeptide chains of the epithelial cell walls are composed of a series of amino acids including cysteine and methionine which contain sulfur side chains. The death of microorganisms or epithelial cells results in degradation of the polypeptide chains into their amino acid components, especially cysteine and methionine. Cysteine and methionine are precursors to the formation of VSC.

Oral malodor not only comes from the posterior dorsal surface of the tongue but also from periodontal pockets. A person with gingivitis or periodontal disease may have increased oral malodor from disintegrated epithelial cells. Epithelial cells turn over faster if inflammation is present. Therefore, a larger number of these dead epithelial cells remain in the oral cavity and will degrade into the malodorous compounds. In addition VSC will also alter the epithelial barrier, permitting penetration of the barrier by antigenic substances.

Oral care compositions, such as mouthwashes and rinses, toothpaste, gels, powders, gums, mouth sprays and lozenges, are directed, completely or in part, towards alleviating the conditions in the mouth which cause malodor, generally by physical means, such as brushing teeth with a dentifrice, or chemical means involving the application of mouthwashes or mouth rinses. Oral care compositions and methods for treating breath malodor using stabilized chlorine dioxide are described in the art. Stabilized chlorine dioxide is, generally, an aqueous solution comprising sodium chlorite and stabilizers to prevent the degradation of the sodium chlorite to molecular chlorine dioxide. Examples of mouthwashes and oral care products comprising stabilized chlorine dioxide are provided by the disclosures of U.S. Pat. Nos. 4,689,215, 4,837,009, 4,696,811, 4,808,389, 4,786,492, 4,788,053, 4,792,442, 4,818,519, 4,851,213, 4,855,135, 4,793,989, 4,855,135, 4,793,989, 4,889,714, 4,925,656, 4,975,285, 4,978,535, 5,200,171, 5,348,734, 5,618,550, and 5,489,435.

Dual phase mouthwash compositions comprising separate chlorite and activator phases are described in U.S. Pat. No. 5,281,412. European Patent Specification 0 565 134 B1 and U.S. Pat. No. 4,986,990 describe two solution mouthwash with a separate chlorite containing solution and activator solution which are mixed prior to use. Other examples of oral care products comprising activators for the delivery of chlorine dioxide or chlorine containing compounds are described in the disclosures of U.S. Pat. Nos. 5,019,402, 4,891,216 and 4,330,531; DE 2,329,753 and WO 95/27472. Additional references relating to chlorine dioxide compositions include U.S. Pat. No. 6,017,515, GB 2,289,841, WO 89/03179 and Japanese references JP 60054311 and JP 60105610.

U.S. Pat. No. 6,077,502 concerns, oral care products having chlorite ion. Examples in U.S. Pat. No. 6,077,502 include: (1) a dual phase mouthwash comprising the chlorite ion in one of the two phases, (2) single phase mouthwash product containing only water, sodium chlorite, sodium carbonate and sodium bicarbonate, and (3) a dry powdered mouth rinse comprising sodium chlorite that requires reconstitution with water prior to use.

Sodium chlorite in an acidic environment, such as the human mouth, releases molecular chlorine dioxide ($ClO_2$). Molecular chlorine dioxide is associated with antibacterial properties and, thus, molecular chlorine dioxide will kill and/or inhibit growth of the bacteria in the mouth which causes breath malodor or halitosis.

Commercially preferred mouthwash and mouth rinse compositions generally comprise excipients, in addition to the active ingredients such as stabilized chlorine dioxide or chlorite ion. Use of stabilized chlorine dioxide in mouthwash, rinses and other oral care compositions comprising excipients is limited, however, by oxidation reactions and the tendency of the chlorine dioxide to cause chlorine odor and yellowing discoloration. This aspect of oral care compositions, including mouthwash and mouth rinse, comprising chlorine dioxide and excipients is a drawback to use as a consumer product and eliminates or limits the ability to package and sell such oral care products in a convenient, consumer friendly package.

To overcome the drawbacks associated with oral care compositions comprising stabilized chlorine dioxide, molecular chlorine and/or chlorite ion and excipients, such oral care compositions and products are generally packaged and sold in either liquid form as a dual phase or two solution system, with one phase/solution comprising the stabilized chlorine dioxide, chlorite ion, molecular chlorine dioxide or precursor and another phase/solution comprising excipients and/or an activator compound, or in a dry form requiring reconstitution prior to use. U.S. Pat. No. 6,077,502 provides an example (Example 4) of a dual phase mouthwash and examples (Examples 7 and 8) of dry powder mouth rinse.

Dual phase/two solution oral care products, such as mouthwashes and rinses, present increased packaging costs and affect consumer acceptance because of the need for the consumer to combine the dual phases/two solutions. For example, the disclosure of WO 95/27472 discusses a kit comprising water, a chlorine-releasing oxidant, a chlorite metal salt and a buffering agent which must be combined prior to use. Also, dry form oral care products require reconstitution with water prior to use which also affects consumer acceptance. A preferred consumer product would enable a mouthwash, mouth rinse or other oral care composition comprising chlorine dioxide and excipients, particularly flavoring agents, to be packaged and sold as a single composition which can be used by the consumer from the packaging without the need to combine the phases or solutions as described in the prior art. There is a need for flavored oral care compositions comprising chlorine dioxide and excipients, and indeed a demand for such products.

It was an object of the invention to develop oral care compositions, including mouthwash and mouth rinse, comprising chlorine dioxide, including the stabilized form, which upon activation, converts to molecular chlorine dioxide, and excipients, including flavoring and coloring agents, which are stable and are not affected by oxidation reactions or exhibit chlorine odor and yellowing discoloration. This can be achieved by use of certain ethoxylated hydrogenated castor oils in the composition which have a hydrophilic side and a hydrophobic side that microencapsulates the flavoring agents in the oral care compositions which prevents oxidation of the flavoring agent by residual free chlorine in the composition. It has also been discovered that such oral care compositions, unexpectedly, do not possess the chlorine odor and yellowing discoloration associated with liquid solutions comprising both chlorine dioxide and excipients, including flavoring agents.

The term "excipient(s)" as used herein, means one or more compatible solid or liquid filler, diluents or non-active or inert ingredients, including flavoring agents and coloring agents, cooling agents, warming agents and numbing agents and encompasses all of the components of the composition except the active ingredient(s). In the present Specification, all parts and percentages are by weight/weight unless otherwise specified.

SUMMARY OF THE INVENTION

The invention pertains to oral care compositions, such as mouthwash, mouth rinse, toothpaste, tooth gels and liquid dentifrices, comprising chlorine dioxide as an active ingredient and excipients, including flavoring agents and ethoxylated hydrogenated castor oil having an ethoxylation number between about 35 and about 60. Prior to activation, the chlorine dioxide is in the form of stabilized chlorine dioxide (e.g. sodium chlorite). The oral care compositions may further comprise pH buffer, sweetener, flavoring agent, coloring agents and/or dyes, glycerin and water. Most preferably, the oral care compositions are in the form of mouthwash or liquid mouth rinse.

The oral care compositions are stable and not characterized by oxidation reactions or chlorine odor and yellowing discoloration on standing. The oral care compositions can be packaged and sold as a single package thus alleviating the discoloration and odor drawbacks in the art and allows for a product that has chlorine dioxide and excipients, such as flavoring agents, and can be packaged, sold and used directly as a single composition rather than a product as described in the prior art which requires a mixing step by the consumer around the time of use.

The method for making the oral care composition comprises formulating a flavor component and a water component. The flavor component comprises the steps of combining liquid ethoxylated hydrogenated castor oil and flavoring agent to form a microemulsion and then adding glycerin. The water component is prepared by combining stabilized chlorine dioxide, pH buffer, sweetener, coloring agents, if desired, and any other excipients. The flavor component and water component are then combined and mixed, until the desired color is obtained or the solution is clear if no coloring agent is included, to form the oral care composition of the invention.

DETAILED DESCRIPTION OF THE INVENTION

The oral care compositions, preferably, comprise:
(a) from about 1 part per million (ppm) to about 75 ppm chlorine dioxide, as an active ingredient,
(b) about 0.25% to about 0.50% pH buffer, preferably a phosphate material,
(c) about 0.05% to about 0.30% sweetener,
(d) about 0.05% to about 0.50% flavoring agent,
(e) about 0.5% to about 5% ethoxylated hydrogenated castor oil having an ethoxylation number between about 35 and about 60,
(f) about 5% to about 20% glycerin,
(g) up to about 0.5% coloring agent and/or dyes, and
(h) about 75% to about 85% water.

Prior to activation, the chlorine dioxide is in the form of stabilized chlorine dioxide. The oral care compositions will not experience oxidation of the flavoring agent and are, unexpectedly, stable not developing chlorine odor or yellowing discoloration, either prior to or at the time of activation.

The oral care compositions may be in the form of mouthwash, mouth rinse, toothpaste, tooth gels and liquid dentifrices but are, preferably mouthwash or mouth rinse compositions. A most preferred mouthwash formulation comprises about 5 ppm chlorine dioxide, about 0.30% sodium monofluorophosphate, about 0.20% saccharin, about 0.25% flavoring agent, about 0.75% ethoxylated hydrogenated castor oil having an ethoxylation number of about 60, about 15% glycerin and about 83.5% water.

Chlorine dioxide is an active ingredient for anti-microbial activity, and is used in oral care products to reduce or eliminate biological activity associated with oral diseases and breath malodor. Chlorine dioxide at an active level of about 1 ppm to about 75 ppm is an effective germicidal in an oral care composition, and chlorine dioxide is an effective and safe germicidal when used in mouthwash and mouth rinse compositions at from about 0.0005% to about 0.2%. Stabilized chlorine dioxide is in the form of a sodium chlorite ($NaClO_2$) solution. When exposed to acidic environments (pH less then about 6.3), such as that of the human mouth, molecular chlorine dioxide forms by the degradation of the sodium chlorite.

The oral care compositions comprise about 1 ppm to about 75 ppm chlorine dioxide in its active form, this correlates to the compositions having from about 0.001% to about 0.1% stabilized chlorine dioxide (e.g. sodium chlorite) prior to activation. Examples of reactions that may take place to release the chlorine dioxide are as follows.

$NaClO_2 + \frac{1}{2}Cl_2 \rightarrow ClO_2 + NaCl$ $5NaClO_2 + 4HCl \rightarrow 4ClO_2 + 5NaCl + 2H_2O$ $2NaClO_2 + HOCl + HCl \rightarrow 2ClO_2 + H_2O + 2NaCl$ Stabilized chlorine dioxide solutions comprising about 2,000 ppm sodium chlorite in deionized water are available under the name ANTHIUM® Dioxide from International Dioxide Incorporated, North Kingstown, R.I., USA, and may be used to advantage in the oral care compositions of the invention.

Prior to activation, the sodium chlorite will degrade to a certain extent resulting in generation of free chlorine, or molecular chlorine dioxide. At activation, the levels will be at about 1 ppm to about 75 ppm. The presence of the free chlorine in oral care compositions having flavoring agents will result in oxidation of the flavoring agent, particularly when the composition comprises flavoring oils. The ethoxylated hydrogenated castor oil having ethoxylation numbers between about 35 and about 60 have hydrophobic and hydrophilic sides. The flavoring agent binds to the hydrophobic side of the ethoxylated hydrogenated castor oil molecule and the hydrophilic side wraps around the flavoring agent and microencapsulates the flavoring agent. The microencapsulated flavoring agent is isolated from residual free chlorine dioxide and chlorine dioxide formed at activation, and will not undergo oxidation which causes degradation of the flavoring agent and a change in the character and nature of the flavor.

The ethoxylated hydrogenated castor oil, which is used in the oral care compositions as a solubilizer, has an ethoxylation number of about 35 to about 60, that is it has an average of about 35 to about 60 ethoxy groups ($C_2H_5O—$) per castor oil molecule. Ethoxylated hydrogenated castor oil can be obtained by reacting hydrogenated castor oil with ethylene oxide. Ethoxylated hydrogenated castor oils are available from BASF, Mount Olive, N.J., USA under the tradename CREMOPHOR® RH. Particularly preferred are CREMOPHOR RH-40 (PEG-40 Hydrogenated Castor Oil with an ethoxylation number of about 40) and CREMOPHOR RH-60 (PEG-60 Hydrogeneated Castor Oil with an ethoxylation number of about 60).

Other solubilizers having different chemical structures than the ethoxylated hydrogenated castor oils having ethoxylation numbers from about 35 to about 60 were evaluated and all resulted in unstable compositions that developed undesirable chlorine odor and/or yellowing discoloration. Block polymers such as Poloxamer 407, available from BASF under the tradename LUTROL® F407, which are polyoxyethylene and polyoxypropylene molecules and PLURACARE® 127 available from BASF which are propylene oxide and ethylene oxide molecules, and Tweens (mixtures of esters of sorbitol and sorbitol anhydride), were evaluated. Based on the evaluations, the inventors theorize, but do not wish to be bound by the theory, that the microencapsulation of the flavoring agent by the ethoxylated hydrogenated castor oil protects the flavor from the chlorine dioxide and other excipients to form a stable composition. It may be that when the flavoring agent is exposed in a composition with chlorine dioxide, a vicious cycle occurs whereby chlorine dioxide, either residual or formed when the pH of the solution decreases, oxidizes the flavoring agent resulting in the breakdown of the flavor leading to total instability and the production of chlorine odor and yellowing discoloration.

Flavoring agents useful for the invention are any food grade or pharmaceutically acceptable flavoring agent. Preferably, the flavoring agent comprises natural flavoring oils, including those selected from the group consisting of oil of peppermint, oil of wintergreen, oil of spearmint, clove bud oil, parsley oil, eucalyptus oil and the like. Combinations of oils can also be used. The flavoring agents may comprise compounds selected from the group consisting of menthol, menthane, anethole, methyl salicylate, eucalyptol, cassia, 1-methyl acetate, sage, eugenol, oxanone, alpha-irisone, marjoram, lemon, orange, propenyl guaethol acetyl, cinnamon, vanilla, thymol, linalool, cinnamaldehyde glycerol acetal and the like, and combinations thereof. The flavoring agent may comprise combinations of natural flavoring oils and other flavoring agents such as the compounds identified above.

Glycerin is used in the oral care compositions, preferably at from about 5% to about 20%. The glycerin acts as a humectant and provides some sweetness to the composition.

The oral care compositions may further comprise up to about 0.5% coloring agents and/or dyes. Any coloring agent or dye that is acceptable for use in foods, pharmaceuticals or other comestible goods, as would be understood to one skilled in the art, may be used. These coloring agents and/or dyes include Food, Drug and Cosmetic (FD&C) colorants including primary FD&C, Blue No. 1, FD&C Blue No. 2, FD&C Green No. 3, FD&C yellow No. 5, FD&C Yellow No. 6, FD&C Red No. 3, and FD&C Red No. 40 and lakes FD&C Blue No. 1, FD&C Blue No. 2, FD&C Yellow No. 5, FD&C Yellow No. 6, FD&C Red No. 2, FD&C Red No. 3, FD&C Red No. 40 and combinations thereof.

A pH buffer must be included in the composition to maintain the pH above about 6.3, preferably from about 6.5 to about 10, most preferably about 6.5 to about 8. Any buffer that creates basic conditions and is acceptable for human consumption can be used in the composition. The preferred buffers are phosphate buffers, particularly trisodium phosphate, sodium monofluorophate, tetrasodium polyphosphate, trisodium pyrophosphate and combinations thereof.

The excipients in the oral care compositions also include sweeteners. Any food grade and/or pharmaceutically acceptable sweetener maybe used, including sucrose, glucose, saccharin, dextrose, levulose, lactose, mannitol, sorbitol, fructose, maltose, xylitol, saccharin salts, thaumatin, aspartame, D-tryptophan, dihydrochalcones, acesulfame and cyclamate salts, especially sodium cyclamate and sodium saccharin, and combinations thereof. The most preferred sweetner is saccharin.

Coolants, warming agents, and numbing agents can be used as optional excipients in the oral care compositions. These may be present in the compositions at a level of from about 0.001% to about 10%, preferably from about 0.1% to about 1%.

The coolant can be any of a wide variety of materials. Included among such materials are carboxamides, menthol, ketals, diols, and mixtures thereof. Preferred coolants are the paramenthan carboxyamide agents such as N-ethyl p-menthane-3-carboxamide, known commercially as "WS-3", N,2,3-trimethyl-2-isopropylbutanamide, known as "WS-23", and mixtures thereof. Additional preferred coolants are selected from the group consisting of menthol, 3-1menthoxypropane-1,2-diol and menthone glycerol. The term menthol and menthyl as used herein include dextra- and levorotatory isomers of these compounds and racemic mixtures thereof. Preferred warming agents include capsicum and nicotinate esters, such as benzyl nicotinate. Preferred numbing agents include benzocaine, lidocaine, clove bud oil, and ethanol.

The oral care compositions comprising chlorine dioxide are formulated with stabilized chlorine dioxide having from about 0.001% to about 0.1% sodium chlorite which correlates to about 1 ppm to about 75 ppm chlorine dioxide when the composition is activated. The method for making the oral care composition comprises formulating a flavor component and water component and then combining the components to form the oral care composition.

The flavor component comprises the ethoxylated hydrogenated castor oil, flavoring agent and glycerin. The ethoxylated hydrogenated castor oil is used in liquid form and, if necessary, must be heated to liquefy prior to combining with the other ingredients. The liquid ethoxylated hydrogenated castor oil having an ethoxylation from about 35 to about 60 is placed in a first means for mixing, such as a mixer, mixing vessel, reactor and the like. The flavoring agent, in liquid form, is then added to the ethoxylated hydrogenated castor oil in the first means for mixing, and mixed to form a microemulsion of ethoxylated hydrogenated castor oil and flavoring agent with the flavoring agent microencapsulated within the ethoxylated hydrogenated castor oil. Glycerin is then added to the first means for mixing and the glycerin is mixed with the microemulsion to form the flavor component.

The water component is prepared in a second means for mixing, which can be any vessel capable of holding liquids and causing the agitation of contents either by stirrer, vibration and the like such as mixer, mixing vessel, reactor and the like. Water is placed into the second means for mixing and then combined with the ingredients liquid stabilized chlorine dioxide (e.g. sodium chlorite solution), pH buffer, sweeteners and the other optional excipients including coloring agents and dyes, cooling agents, numbing agents and warming agents. The water and ingredients are then mixed to form the water component.

The water component is then combined with the flavor component in the first means for mixing and the water component and flavor component are mixed. Mixing of these components occurs until the appropriate color is achieved if coloring agents and/or dyes are used, or until the solution is clear if no color agents or dyes are used to form the oral care composition. The resulting oral care composition is an oil-in-water emulsion.

The weight of ingredients and mixing times, temperatures and other variables will be dependent on the amount of oral care composition made, as can be readily determined by one skilled in the art. In the preferred embodiment of the invention, the ingredients employed, however, comprise sufficient amounts of ingredients to make an oral care composition comprising about 0.001% to about 0.1% stabilized chlorine dioxide, about 0.25% to about 0.5% buffer, about 0.05% to about 0.30% sweetener, about 0.05% to about 0.5% flavoring agent, about 1.5% to about 5% ethoxylated hydrogenated castor oil having an ethoxylation number between about 35 and about 60, about 5% to about 20% glycerin, up to about 0.5% coloring agent and/or dye, about 75% to about 85% water and other excipients.

The oral care compositions may be in the form of mouthwash, mouth rinse, toothpaste, gels, liquid tooth dentifrice and the like. The preferred compositions are mouthwashes and/or mouth rinses. Oral care products comprising the oral care compositions can also include the usual components, as understood in the art, for the particular product. For example, toothpaste and tooth gel products will generally require carrier components such as thickening agents to provide desirable consistency and humectants to prevent the tooth paste from hardening. Acceptable thickening agents include polymeric polyester compounds, hydroxyethyl cellulose, natural gums (e.g. gum karaya, gum arabic, gum tragacanth) and the like. The thickening agents may also comprise colloidal magnesium silicate or finally divided silica for texture. Suitable humectants include glycerin, sorbitol, edible polyhydric alcohols and the like.

The oral care compositions are stable and will not experience oxidation of the flavoring agent or undergo generation of chlorine odor or yellowing discoloration. Thus, the oral care compositions can be packaged, sold, stored, and used as a single oral care package, that is packaging wherein all of the components, including the chlorine dioxide (or stabilized chlorine dioxide) and excipients are in a single container, such as a bottle or tube. For example, in the embodiment of the invention involving mouthwash or mouth rinse, the composition can be packaged in a single glass or plastic container for commercial sale to the consumer to use directly from the packaging, compared to a dual phase/two solution composition of the prior art, where the chlorite phase/solution and excipient phase/solution are packaged in different vessels requiring the consumer or dental health care professional to combine the phases/solutions prior to use.

EXAMPLES

Example 1

To ascertain the compatibility between sodium chlorite and solubilizers, a number of solubilizers, including ethoxylated hydrogenated castor oil, were evaluated with stabilized chlorine dioxide. An ethoxylated hydrogenated castor oil, CREMOPHOR RH-60 from BASF, pH buffer and CLOSYS II®, which is a mouth rinse solution comprising 0.125% chlorine dioxide in active form available from Raintree Essix, Inc., New Orleans, La., USA, were combined in a glass jar and shaken to form a solution. Poloxamer 407 from BASF (LUTROL®F407) and PLURACARE®127 were separately combined in glass jars with pH buffer and CLOSYS II and shaken to form separate solutions. The glass jars were then stored in at 50° C. for one week.

After one week of storage the jars were observed for yellowing discoloration and chlorine odor. The solution comprising CREMOPHOR RH-60 did not possess yellowing discoloration or exhibit a chlorine odor. The samples having Poloxamer 407 or PLURACARE®127 had a yellow color to greenish yellow color and chlorine odor.

Example 2

A mouthwash solution comprising 0.01% stabilized chlorine dioxide (ANTHIUM Dioxide from International Dioxcide, 2,000 ppm sodium chlorite solution), 0.75% CREMOPHOR RH-60 from BASF, 0.30% trisodium phosphate (pH buffer), 0.25% flavoring agent comprising oil of peppermint, 0.20% saccharin, 15% glycerin and 83.49% water was prepared. The formulation correlates to about 2 ppm chlorine dioxide in active form.

The solution was prepared by first formulating a flavor component by combining the CREMOPHOR RH-60 in liquid form and the flavoring agent in a first mixing vessel and mixing to form a microemulsion. Then, the glycerin was added to the first mixing vessel and mixed with the microemulsion. In a second mixing vessel the water, stabilized chlorine dioxide, trisodium phosphate and saccharin were combined and mixed to form a water component. The water component was then added to the flavor component in the first mixing vessel and mixed until the mouthwash solution was clear to form the oral care composition. The oral care composition formed was an oil-in-water emulsion and had a pH of 7.

Samples of the mouthwash solution were stored in glass jars at 50° C. for one week and then observed for yellowing discoloration and chlorine odor. None of the samples had yellowing discoloration or exhibited chlorine odor.

Samples of the mouthwash solution were stored in glass jars at ambient temperature for nine months to assess flavor stability. After nine months the samples were activated and titrated for $ClO_2$ using standard titration methods. The titration procedure resulted in nearly 100% recovery of $ClO_2$ which indicates that the $ClO_2$ did not undergo significant oxidation reactions. The samples were also subjected to standard gas chromatography analysis for the volatile flavoring constituents. The gas chromatography analysis revealed that the volatile flavoring constituents did not undergo oxidation reactions.

What is claimed is:

1. An oral care composition comprising:
   (a) chlorine dioxide,
   (b) ethoxylated hydrogenated castor oil having an ethoxylation number of about 35 to about 60,
   (c) flavoring agent,
   (d) pH buffer,
   (e) sweetener,
   (f) glycerin, and
   (g) water;
   wherein the pH of the composition is above about 6.3 said oral care composition being an oil-in-water emulsion said chlorine dioxide being stabilized chlorine dioxide in the form of about 0.001% to about 0.1% of a sodium chlorite solution, which, when exposed to the mouth, pH less than about 6.3, forms about 1 ppm to about 75 ppm molecular chlorine dioxide by the degradation of the sodium chlorite, said ethoxylated hydrogenated castor oil and said flavoring agent both being in liquid form and admixed to form a microemulsion of ethoxylated hydrogenated castor oil and flavoring agent with said flavoring agent microencapsulated within said ethoxylated hydrogenated castor oil and said glycerin mixed with said microemulsion to form a flavor component, said microencapsulation forming a stable composition protecting the flavor from free chlorine and/or chlorine dioxide oxidation, production of chlorine odor and yellowing discoloration.

2. The oral care composition of claim 1 comprising:
   (a) about 1 ppm to about 75 ppm of the chlorine dioxide,
   (b) about 0.5% to about 5% of the ethoxylated hydrogenated castor oil having an ethoxylation number of about 35 to 60,
   (c) about 0.05% to about 0.50% of the flavoring agent,
   (d) about 0.25% to about 0.50% of the pH buffer,
   (e) about 0.05% to about 0.30% of the sweetener,
   (f) about 5% to about 20% of the glycerin; and
   (g) about 75% to about 85% of the water.

3. The oral care composition of claim 1 further comprising coloring agent and/or dye.

4. The oral care composition of claim 3 comprising up to about 0.5% coloring agent and/or dye.

5. The oral care composition of claim 1 wherein the flavoring agent comprises natural flavoring oil.

6. The oral care composition of claim 5 wherein the natural flavoring oil is selected from the group consisting of oil of peppermint, oil of wintergreen, oil of spearmint, clove bud oil, parsley oil, eucalyptus oil and combinations thereof.

7. The oral care composition of claim 1 wherein the flavoring agent comprises compounds selected from the group consisting of menthol, menthane, anethole, methyl salicylate, eucalyptol, cassia, 1-methyl acetate, sage, eugenol, oxanone, alpha-irisone, marjoram, lemon, orange, propenyl guaethol acetyl, cinnamon, vanillin, thymol, linalool, cinnamaldehyde glycerol acetyl and combinations thereof.

8. The oral care composition of claim 1 further comprising warming agents.

9. The oral care composition of claim 1 further comprising cooling agents.

10. The oral care composition of claim 1 further comprising numbing agents.

11. The oral care composition of claim 1 wherein the buffer is selected from the group consisting of trisodium phosphate, sodium monofluorophosphate tetrasodium polyphosphate, trisodium pyrophosphate and combinations thereof.

12. The oral care composition of claim 1 wherein the sweetener is selected from the group consisting of sucrose, glucose, saccharin, dextrose, levulose, lactose, mannitol, sorbitol, fructose, maltose, xylitol, saccharin salts, thaumatin, aspartame, D-tryptophan, dihydrochalcones, acesulfame, cyclamate salts and combinations thereof.

13. A method for making the oral care composition of claim 1 comprising the steps of:
   (1) preparing a flavor component in a first means for mixing by mixing liquid flavoring agent and liquid ethoxylated hydrogenated castor oil having an ethoxylation number of about 35 to about 60 to form a microemulsion, and then mixing the microemulsion with glycerin,
   (2) preparing a water component in a second means for mixing by mixing water, liquid stabilized chlorine dioxide, pH buffer, sweeteners and, optionally, other excipients, and
   (3) combining the flavor component and the water component and mixing to obtain the oral care composition.

14. The method of claim 13 wherein the other excipients are selected from the group consisting of coloring agents and/or dyes, cooling agents, warming agents, numbing agents and combinations thereof.

15. The method of claim 13 wherein the flavoring agent comprises natural flavoring oil.

16. The method of claim 15 wherein the natural flavoring oil is selected from the group consisting of oil of peppermint, oil of wintergreen, oil of spearmint, clove bud oil, parsley oil, eucalyptus oil and combinations thereof.

17. The method of claim 13 wherein the flavoring agent comprises compounds selected from the group consisting of menthol, menthane, anethole, methyl salicylate, eucalyptol, cassia, 1-methyl acetate, sage, eugenol, oxanone, alpha-irisone, marjoram, lemon, orange, propenyl guaethol acetyl, cinnamon, vanillin, thymol, linalool, cinnamaldehyde glycerol acetyl and combinations thereof.

18. An oral care package comprising the oral care composition of claim 1 and a container.

19. An oral care package of claim 18 in the form of a mouthwash or mouth rinse.

20. The oral care composition of claim 1, wherein the pH of the composition is about 6.5 to about 10.

21. The oral care composition of claim 20, wherein the pH of the composition is about 6.5 to about 8.

* * * * *